United States Patent
Kataoka et al.

(10) Patent No.: US 10,758,188 B2
(45) Date of Patent: Sep. 1, 2020

(54) STROKE DETECTION AND PREVENTION SYSTEM AND METHOD

(71) Applicant: NTT Innovation Institute, Inc., Palo Alto, CA (US)

(72) Inventors: Yasuyuki Kataoka, Palo Alto, CA (US); Ravi Srivatsav, Palo Alto, CA (US)

( * ) Notice: Subject to any disclaimer, the term of this patent is extended or adjusted under 35 U.S.C. 154(b) by 208 days.

(21) Appl. No.: 15/709,020

(22) Filed: Sep. 19, 2017

(65) Prior Publication Data

US 2018/0078213 A1    Mar. 22, 2018

Related U.S. Application Data

(60) Provisional application No. 62/396,597, filed on Sep. 19, 2016.

(51) Int. Cl.

| | |
|---|---|
| *A61B 5/00* | (2006.01) |
| *A61B 5/11* | (2006.01) |
| *A61B 5/22* | (2006.01) |
| *G16H 80/00* | (2018.01) |
| *G16H 50/20* | (2018.01) |
| *G16H 10/60* | (2018.01) |
| *G16H 50/30* | (2018.01) |
| *G06F 19/00* | (2018.01) |
| *A61B 5/0205* | (2006.01) |

(52) U.S. Cl.
CPC .......... *A61B 5/7275* (2013.01); *A61B 5/112* (2013.01); *A61B 5/1124* (2013.01); *A61B 5/4064* (2013.01); *A61B 5/4803* (2013.01); *A61B 5/7465* (2013.01); *G06F 19/3418* (2013.01); *G16H 10/60* (2018.01); *G16H 50/20* (2018.01); *G16H 50/30* (2018.01); *G16H 80/00* (2018.01); *A61B 5/0205* (2013.01); *A61B 5/224* (2013.01)

(58) Field of Classification Search
CPC .......... A61B 5/103; A61B 5/11; A61B 5/112; A61B 5/4064; A61B 5/4803; A61B 5/224; A61B 5/72; A61B 5/7235; A61B 5/7264; A61B 5/7271; A61B 5/7282
See application file for complete search history.

(56) References Cited

U.S. PATENT DOCUMENTS

| | | | |
|---|---|---|---|
| 7,244,231 B2 * | 7/2007 | Dewing | A61B 5/0002 600/300 |
| 7,912,698 B2 | 3/2011 | Statnikov et al. | |
| 8,135,718 B1 | 3/2012 | Das et al. | |
| 2002/0052858 A1 | 5/2002 | Goldman et al. | |
| 2002/0138492 A1 | 9/2002 | Kil | |
| 2004/0044273 A1 * | 3/2004 | Keith | A61B 5/224 600/300 |
| 2006/0037080 A1 | 2/2006 | Maloof | |
| 2008/0294019 A1 | 11/2008 | Tran | |
| 2009/0028141 A1 | 1/2009 | Vu Duong et al. | |
| 2009/0157057 A1 | 6/2009 | Ferren et al. | |

(Continued)

OTHER PUBLICATIONS

Auto-WEKA webpage printed Feb. 17, 2015 (2 pages).

(Continued)

*Primary Examiner* — Eric F Winakur

(57) ABSTRACT

A stroke detection and prevention system and method are provided in which there may be one or more phases of detection using devices in which the phases include user-friendly, less accurate tests to less user-friendly, more accurate tests.

18 Claims, 9 Drawing Sheets

(56) References Cited

U.S. PATENT DOCUMENTS

| | | |
|---|---|---|
| 2009/0254992 A1 | 10/2009 | Schultz et al. |
| 2010/0183211 A1 | 7/2010 | Meetz et al. |
| 2011/0299420 A1 | 12/2011 | Waggener et al. |
| 2013/0111036 A1 | 5/2013 | Ozawa et al. |
| 2014/0122370 A1 | 5/2014 | Jamal et al. |
| 2014/0163640 A1 | 6/2014 | Edgerton et al. |
| 2014/0201374 A1 | 7/2014 | Ashwood-Smith |
| 2014/0219096 A1 | 8/2014 | Rabie et al. |
| 2014/0317261 A1 | 10/2014 | Shatzkamer et al. |
| 2014/0317293 A1 | 10/2014 | Shatzkamer |
| 2015/0082308 A1 | 3/2015 | Kiess et al. |
| 2015/0227964 A1 | 8/2015 | Yan et al. |
| 2015/0288767 A1 | 10/2015 | Fargano et al. |
| 2015/0317169 A1 | 11/2015 | Sinha et al. |
| 2015/0326535 A1 | 11/2015 | Rao et al. |
| 2015/0333979 A1 | 11/2015 | Schwengler et al. |
| 2015/0381423 A1 | 12/2015 | Xiang |
| 2016/0006642 A1 | 1/2016 | Chang et al. |
| 2016/0050161 A1 | 2/2016 | Da et al. |
| 2016/0057234 A1 | 2/2016 | Parikh et al. |
| 2016/0154960 A1 | 6/2016 | Sharma et al. |
| 2016/0180042 A1* | 6/2016 | Menon .................. G06F 19/321 705/2 |
| 2016/0350846 A1* | 12/2016 | Dintenfass .............. G06F 19/00 |

OTHER PUBLICATIONS

Ayat, N.E.; Cheriet, M.; Suen, C.Y.; "Automatic Model Selection for the optimization of SVM Kernels," Mar. 21, 2005 (35 pages).

Brodley, Carla E., "Addressing the Selective Superiority Problem: Automatic Algorithm/Model Class Selection," (1993) (8 pages).

Chapelle, Olivier; Vapnik, Vladimir; Bousquet, Olivier; Mukherjee, Sayan; "Choosing Multiple Parameters for Support Vector Machines," Machine Learning, 46, 131-159, 2002 © 2002 Kluwer Academic Publishers, Manufactured in The Netherlands.

Lee, Jen-Hao and Lin, Chih-Jen, "Automatic Model Selection for Support Vector Machines," (2000).

Smith, Michael R.; Mitchell, Logan; Giraud-Carrier, Christophe; Martinez, Tony; "Recommending Learning Algorithms and Their Associated Hyperparameters," Jul. 7, 2014 (2 pages).

Thornton, Chris. Thesis: "Auto-WEKA: Combined Selection and Hyperparameter Optimization of Supervised Maching Learning Algorithms," Submitted to the University of British Columbia, Mar. 2014 (75 pages).

Thornton, Chris; Hutter, Frank; Hoos, Holger H.; Leyton-Brown, Kevin. "Auto-WEKA: Combined Selection and Hyperparameter Optimization of Classification Algorithms," Mar. 2013 (9 pages).

Wolinski, Christophe; Kuchcinski, Krzysztof. "Automatic Selection of Application-Specific Reconfigurable Processor Extensions." Design, Automation & Test in Europe Conference (DATE '08), Mar. 2008, Munich, Germany, pp. 1214-1219 (7 pages).

Workshop Handout edited by Joaquin Vanschoren, Pavel Brazdil, Carlos Soares and Lars Kotthoff, "Meta-Learning and Algorithm Selection Workshop at ECAI 2014," MetaSel 2014, Aug. 19, 2014 (66 pages).

* cited by examiner

STROKE DETECTION AND PREVENTION SYSTEM AND METHOD

PRIORITY CLAIMS/RELATED APPLICATIONS

This application claims priority under 35 USC 120 and claims the benefit under 35 USC 119(e) to U.S. Provisional Patent Application Ser. No. 62/396,597 filed on Sep. 19, 2016 and entitled "Stroke Detection and Prevention System and Method", the entirety of which is incorporated herein by reference.

FIELD

The disclosure relates generally to a system and method for detection and prevention of strokes.

BACKGROUND

Every year, 15 million people worldwide have a stroke. Of these, 6 million people die each year so that every six seconds, a life is taken by a stroke. However, 80% of strokes are entirely preventable. Treatments already exist for strokes, some involving surgery, but only 3-4% of patients receive these treatments. This means that 96% of the world's population would greatly benefit from a solution for the detection and prevention of strokes.

Today, patients do not recognize the disease until it gets serious. Thus, although the symptoms of some diseases or medical conditions like strokes, heart attacks, and diabetes are well known, many people do not go to doctor until the situation gets serious because of cost, laziness, over-confidence, lack of time, or some other excuse.

Thus, it is desirable to provide a solution for the detection and prevention of strokes and it is to this end that the disclosure is directed.

DETAILED DESCRIPTION OF ONE OR MORE EMBODIMENTS

The disclosure is particularly applicable to a stroke detection and protection system and method using gait analysis, speech analysis, arm test and telemedicine for the detection and prevention of a stroke and it is in this context that the disclosure will be described. It will be appreciated, however, that the system and method has greater utility since the system and method for stroke detection and prevention may be implemented using other phases than those described in the implementation below and those other phases are within the scope of the disclosure. Furthermore, although the implementation described below is directed to stroke detection and prevention, the system and method can also be modified to be used to detect and/or prevent other health issues/disease/conditions.

The proliferation of wearable and assistant Human Internet of Things (HIoT) devices may be used by the stroke detection and prevention system and method as part of the solution that can save the lives of many people around the world through the detection and prevention of stroke. The system and method may also use data analytics.

Figure 1:
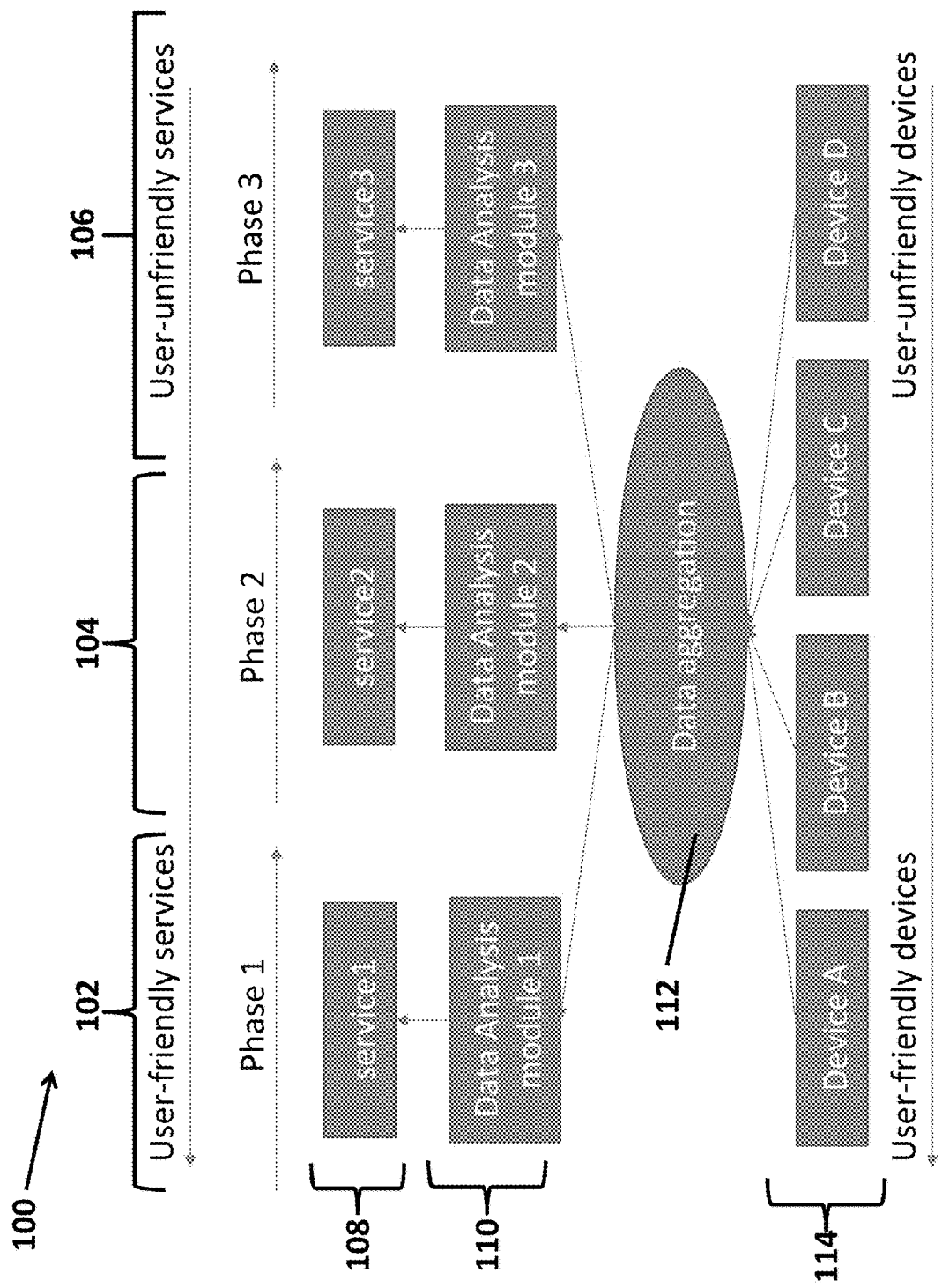
FIG. 1 illustrates a stroke detection and prevention system.

FIG. 1 illustrates a stroke detection and prevention system 100 that may include multi-dimensional data collection and aggregation. The system may include one or more phases of detection/analysis that may be used to help to detect and prevent strokes. The different phases may range from more user-friendly services in phase 1 102, to phase 2 104 and then to user-unfriendly services in phase 3 106. Each phase 102-106 may include a service 108, such as service 1 for phase 1, etc. and a data analysis module 110 coupled to the service that receives data from the service. Each of the phases 102-106 may be implemented using a computer system element that performs the processes of each phase as described below in more detail.

The analyzed data from each phase may be aggregated by a data aggregation component 112. The data aggregation component 112 may in turn couple to and exchange data with one or more devices 114 in which the devices in each phase may range from user-friendly devices in phase 1 to user-unfriendly device in phase 3.

The services 108, the data analysis modules 110 and the data aggregation engine 112 (collectively a stroke detection and prevention system) shown in FIG. 1 may each be implemented in hardware or software or a combination of hardware and software. When the stroke detection and prevention system and the different elements are implemented in software, each element may be a plurality of lines of computer code/instructions that may be executed by a processor of the stroke detection and prevention computer system (that also have a memory) and the processor is thus configured to perform the processes that are described in more detail below for each element. When the stroke detection and prevention system and the different elements are implemented in hardware, each element may be a hardware device, such as a memory, microcontroller, etc., that may perform the processes that are described in more detail below for each element.

Figure 2:
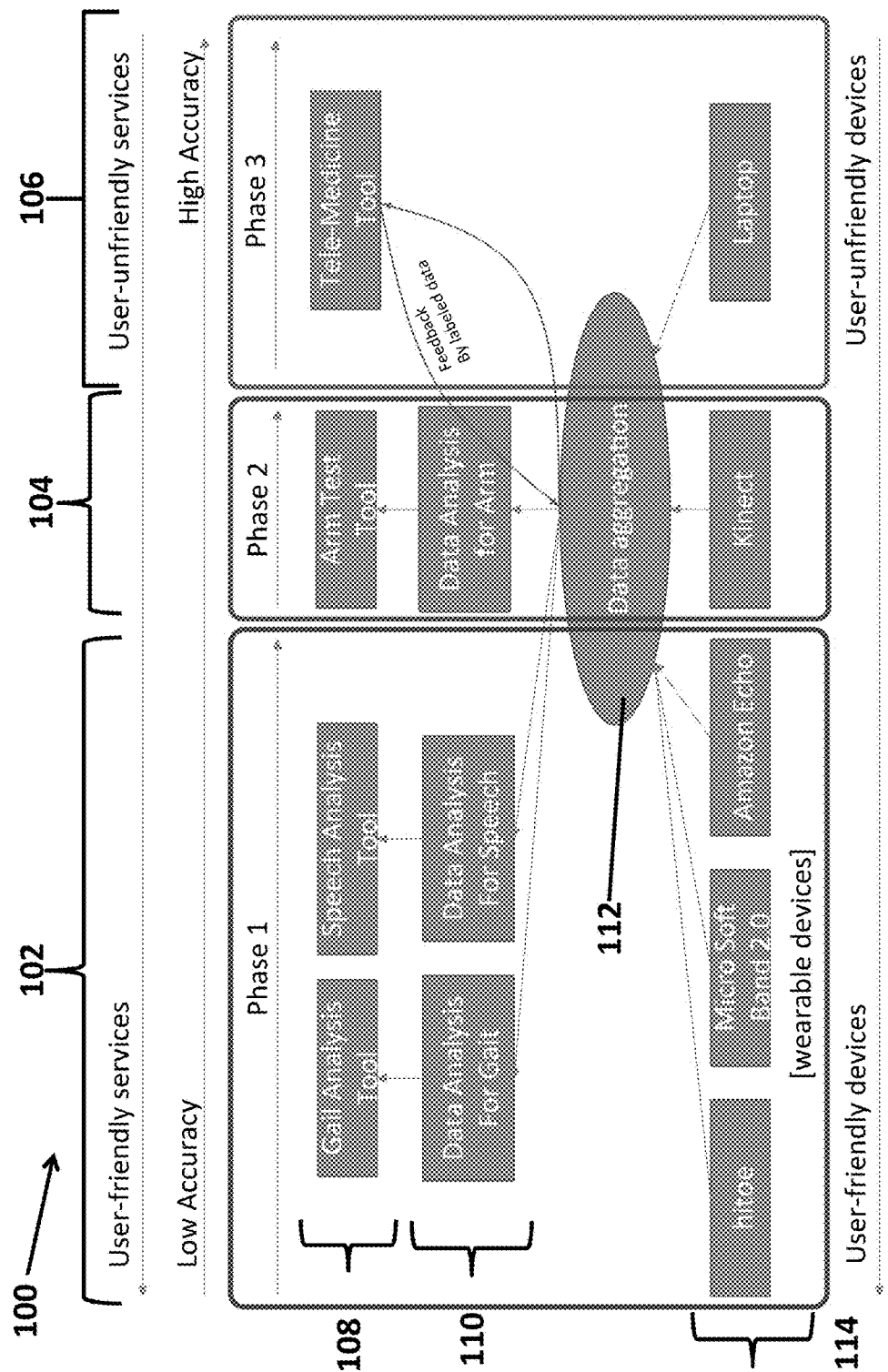
FIG. 2 illustrates an embodiment of the stroke detection and prevention system.

FIG. 2 illustrates an embodiment of the stroke detection and prevention system 100 with examples of the services 108 and phases 102-106 that may be used for stroke detection and prevention. In the embodiment shown in FIG. 2, phase 1 102 (user friendly services) may include gait analysis and speech analysis (both of which may be done at home), phase 2 104 may include an arm test (that may also be done at home) and phase 3 106 may include telemedicine in which one or more doctors may use videoconferencing to examine patients in their homes. The gait analysis, speech analysis and arm test may be implemented using machine learning algorithms. A web-based dashboard provides doctors with real-time data from their patients' HIoT devices and the system allows the one or more doctors to label the data from the devices and the phases. The system may also use machine learning algorithms to improve diagnostic accuracy. As shown in FIG. 2, the phase 1 102 may be lower accuracy, but more user-friendly devices while the phase 3 106 may be higher accuracy, but less user-friendly devices.

The system 100 may use various different types of computing devices 114 to interface with the user as part of the stroke detection and prevention system. For example, the system may use one or more internet of things (IoT) devices for healthcare use at home. The devices 114 may include wearable sensing fabrics and band-type devices such as NTT hitoe, Microsoft Band, Apple Watch, and Fitbit trackers, assistant devices such as Amazon Echo, Siri, and Docomo Shabette Concier, game devices such as Kinect and Leap and/or sensing devices such as blood pressure sensors and weight sensors. There are even IoT toilets that track patients' excreta. In the example shown in FIG. 2, the phase 1 portion 102 may use different wearable devices and/or assistant devices, the phase 2 portion 104 may use game device and the phase 3 portion 106 may use a computing device, such as a laptop computer, a personal computer, a tablet computer and similar devices. Each different type of computing device 114 may capture a different type of health data that may be used for stroke detection. For example, the Microsoft band and hitoe may capture data about a person swinging their arms or pace of walking that is one type of health data that may be used to detect a stroke. As another example, a Microsoft Kinect device may capture data about arm strength of a user that is another type of health data that may be used to detect a stroke. As yet another example, a patient may provide verbal or visual data about stroke indicators to a doctor during a telemedicine session and those stroke indicators are another type of health data that may be used to detect a stroke.

One or more of the devices 114 may also include a display and input/output devices that allow the user to interact with the stroke detection and prevention system. For example, the user may be able to upload the various test data described below, conduct the telemedicine session as described below and receive data about the analysis being performed by the system.

The system may use the above devices 114 to proactively diagnose stroke symptoms so that a patient can seek medical help before a stroke occurs. For example, the system may collect and aggregate a patient's data from the devices 114 to diagnose stroke symptoms and may also collect patient data labeled by the doctor. The system may also identify multiple stroke symptoms with each symptom being identified by analysis of multiple data streams from multiple devices. The system may guide the patient through the stroke detection phases.

Figure 3:
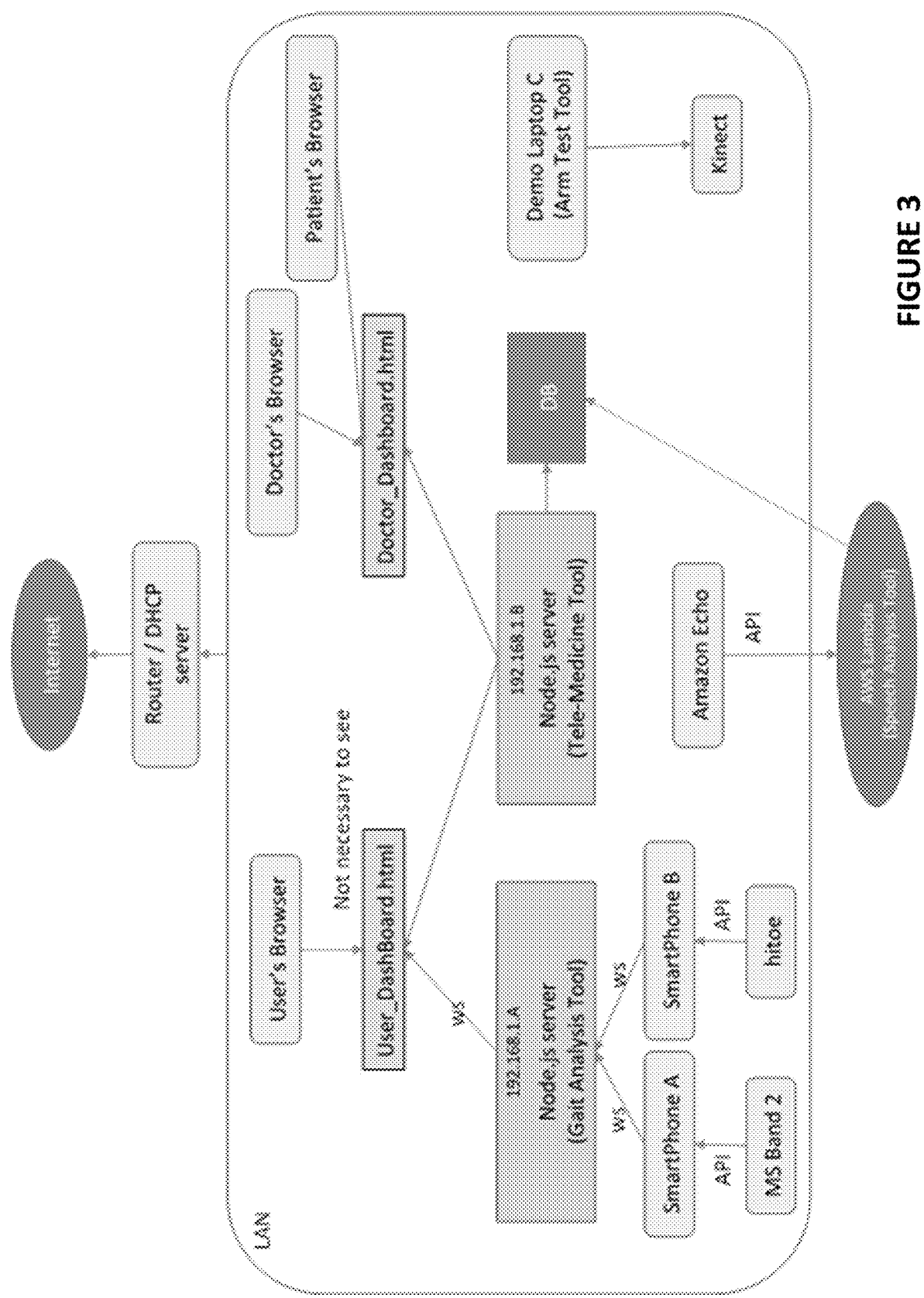
FIG. 3 illustrates an example of an implementation of the stroke detection and prevention system.

In the system, the gait analysis may use a gait analysis tool as a service 108 (based on the data from the devices 114) and a gait data analysis module 110 whose gait data and analyzed gait data is provided to the data aggregator 112. The speech analysis may use a speech analysis tool as a service 108 (based on the data from the devices 114) and a speech data analysis module 110 whose speech data and analyzed speech data is provided to the data aggregator 112. The arm test may use an arm test tool as a service 108 (based on the data from the devices 114) and an arm test data analysis module 110 whose arm test data and analyzed arm test data is provided to the data aggregator 112. The tele-medicine in phase 3 106 may use a tele-medicine tool a service 108 and may exchange data with the data aggregator 112. The doctor using the tele-medicine tool may label patient data and feed that data based to the data aggregator 112. The patient may use a computing device, such as laptop, tablet, etc. to interact with the tele-medicine tool. FIG. 3 illustrates an implementation of the system including the servers, webpages, devices 114, APIs and databases.

Gait Analysis

Gait analysis examines the way a person walks. Multimodal data analysis from multiple devices 114 can detect symptoms such as people walking without swinging their arms (Microsoft Band) or a person walking slowly or out of balance (hitoe). Multimodal data analysis implements an algorithm that computes an Anomaly Score(s) based on the input collected from the devices 114, although other algorithms may also be used.

The anomaly score, s, may be determined using the following equation:

$$s = 1/3 * (x+y+z)$$

where x: measures body balance (measurement obtained through the Hitoe API)

v: measures arm swinging (measurement is obtained through the Microsoft Band API)

z: measures cadence (measurement is obtained through the Hitoe API).

Figure 4:
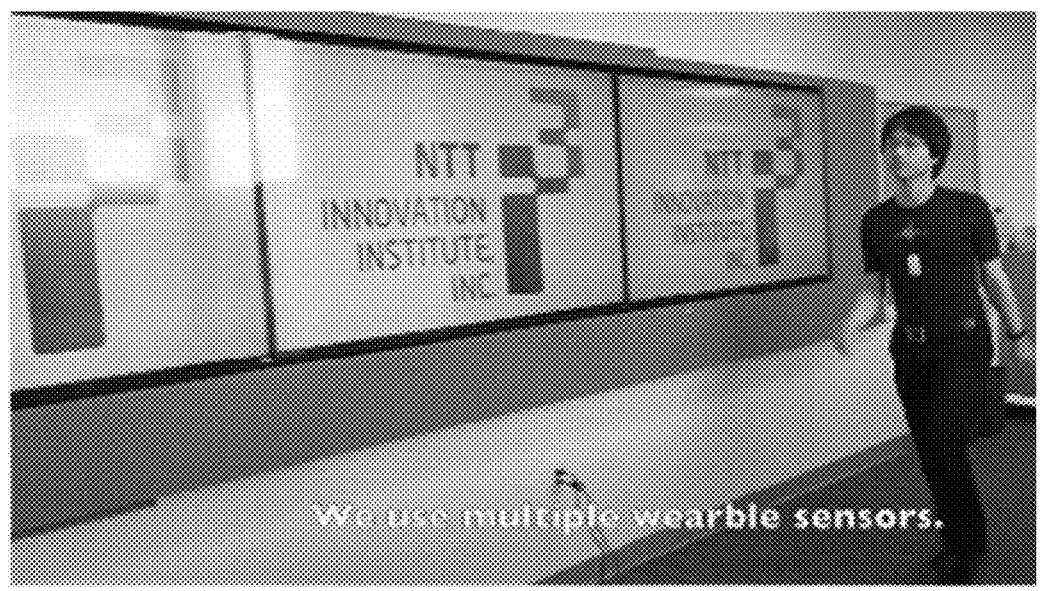
FIG. 4 illustrates the gait analysis of the stroke detection and prevention system.
Figure 5:
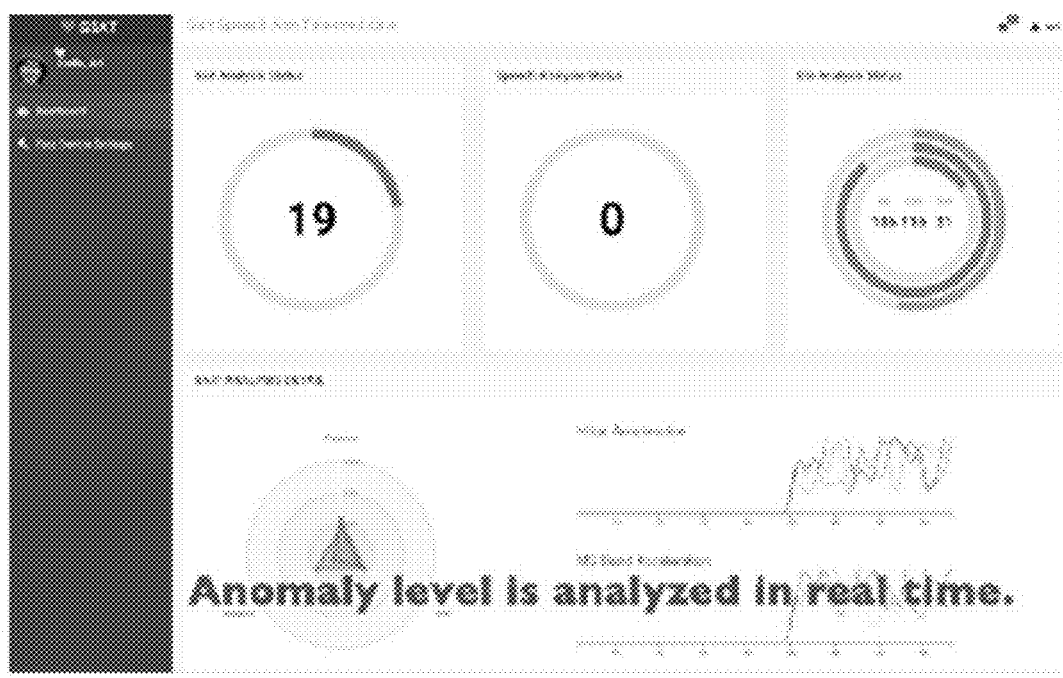
FIGS. 5 and 6 illustrate examples of the user interface of the gait analysis portion of the stroke detection and prevention system.
Figure 6:
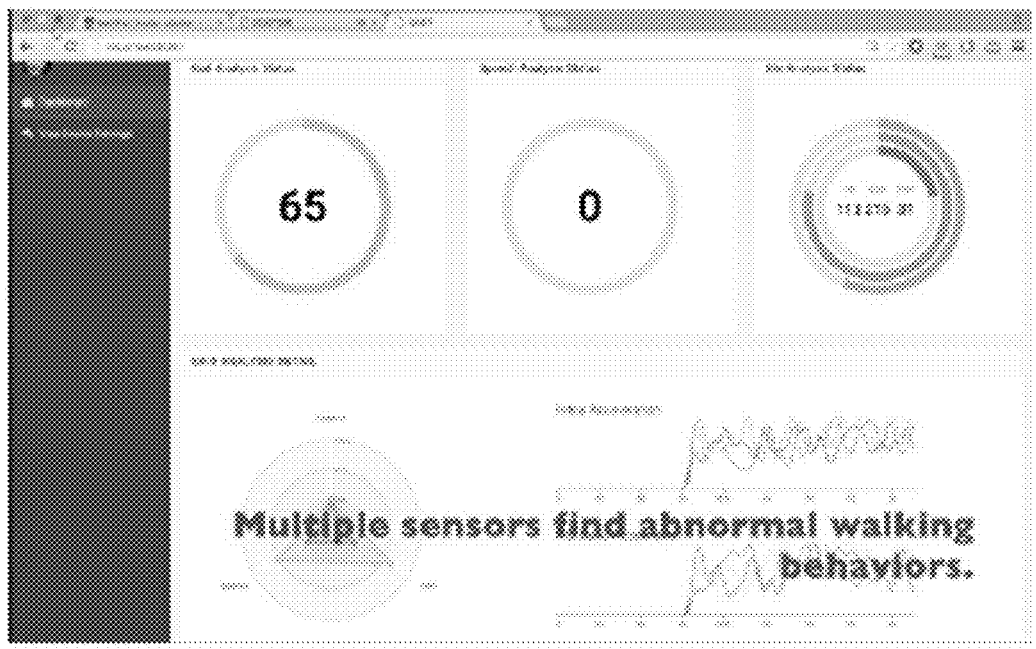

For example, a user may wear two devices/sensors as shown in FIG. 4. In one example, the user may wear a Hitoe fabric sensor which measures balance and cadence and a Microsoft Band 2.0 sensor, which measures arm swing. FIG. 5 shows an example of a web-based gait dashboard that shows the following: a GAIT anomaly score of 19, ECG or Acceleration data in real-time and the gait feature that indicates a problem (bottom-left chart in FIG. 5). As shown in FIG. 6, if the patient walks without swinging an arm, slowly, or in an unbalanced manner, the system detects this condition and shows it in the chart as an abnormal condition.

Speech Analysis

The devices 114, such as medical IoT devices, can be used for speech analysis. For example, a user talks to an assistant device, such as Amazon Echo, on a daily basis. If the speech quality is distorted, the device can take that as a symptom of stroke. Depending on the voice quality analysis, the device can calculate the anomaly score.

The following is a sample scenario.

User: "Tell me my condition."

Assistant device: "You have done 7800 steps today. Looks good to me. How do you feel now, Yasu?"

[Normal case]

User: "I am fine!"

Assistant device: "Great to hear that. Enjoy your day!"

[Abnormal case]

User: "umm, I am okay." (with weird utterance)

Assistant device: "Umm. It sounds like you are not well. Your recent walking behavior might be abnormal. Please take medicine or perform the Body Balance test. Can you lift your arms together to 90 degree and keep it there for 5 seconds? Microsoft Kinect will check your performance."

Figure 7:
FIGS. 7 and 8 illustrate examples of the speech analysis that is part of the stroke detection and prevention system.
Figure 8:

As shown in FIG. 7, because the user's activity information is aggregated in stroke detection and prevention system, assistant devices can determine the health condition of the user based on factors like the user's quality of sleep, exercise history, and work history. As shown in FIG. 8, when the assistant device asks a common question like "How are you?" the user's response is analyzed in the back-end to determine the quality of speech and whether there is an anomaly. If both gait and speech analysis show stroke symptoms, the system prompts the user to perform the Phase 2 tests.

Arm

The arm test is the gold standard when it comes to testing patients for strokes. According to a study published in 2003, doctors are encouraged to perform the arm test because of its high accuracy in diagnosing strokes. The test may be as follows:

"Lift the patient's arms together to 90 degree if sitting, 45 degree if supine and ask them to hold the position for 5 seconds then let go. Does one arm drift down or fail rapidly? If one arm drifts down or fails, note whether it is the patient's left or right arm." Harbison, J., Hossain, O., Jenkinson, D., Davis, J., Louw, S. J., & Ford, G. A. (2003). Diagnostic accuracy of stroke referrals from primary care, emergency room physicians, and arribulance staff using the face arm speech test. Stroke, 34(1), 71-76.

According to a study published in 2004, arm weakness in the arm test provides 98% certainty that the patient is exhibiting a stroke symptom. "Complete agreement for each neurological sign was: facial weakness, 78%; arm weakness, 98%; and speech disturbance, 89%." Nor, A. M., McAllister, C., Louw, S. J., Dyker, A. G., Davis, M., Jenkinson, D., % Ford, G. A. (2004). Agreement between ambulance paramedic- and physician-recorded neurological signs with Face Arm Speech Test (FAST) in acute stroke patients. Stroke, 35(6), 1355-1359.

It is worthy to note that both studies demonstrate that arm weakness is the most reliable lowed by speech impairment, and facial weakness. One of the devices that can be used for the arm test and can be integrated with the system 100 is Microsoft Kinect, which can track arm movement. For example, if a user can hold both arms for 5 seconds, no action is taken. However, if one arm drops within 5 seconds, the system 100 may send a warning message. If a user cannot hold both arms, the system 100 may send a message indicating presence of a dangerous condition that requires immediate medical attention.

Figure 9:
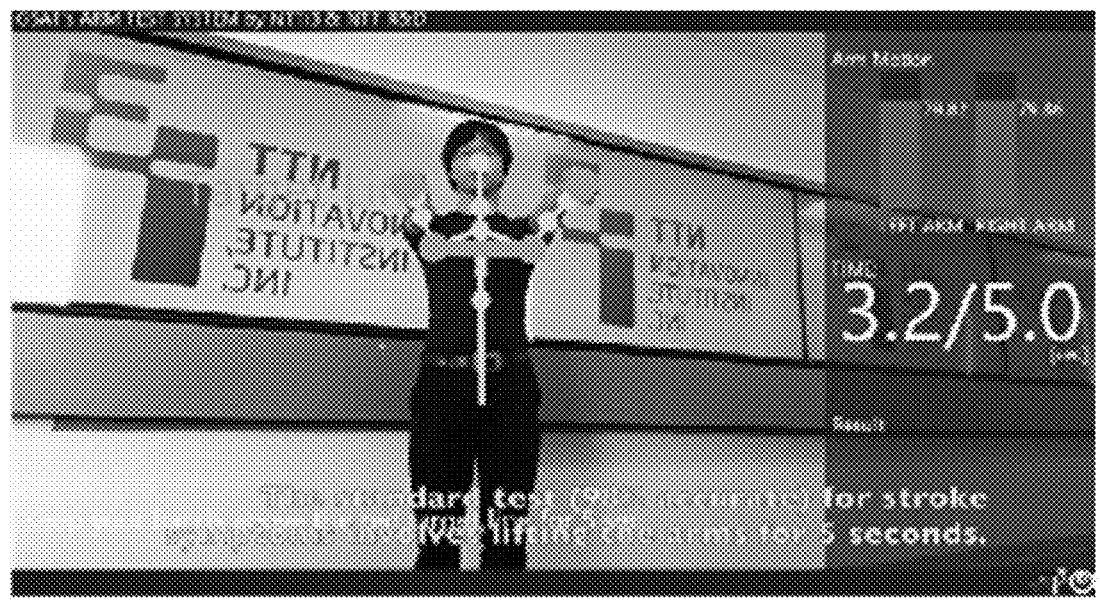
FIGS. 9-12 illustrate examples of the arm test that is part of the stroke detection and prevention system.
Figure 10:
Figure 11:
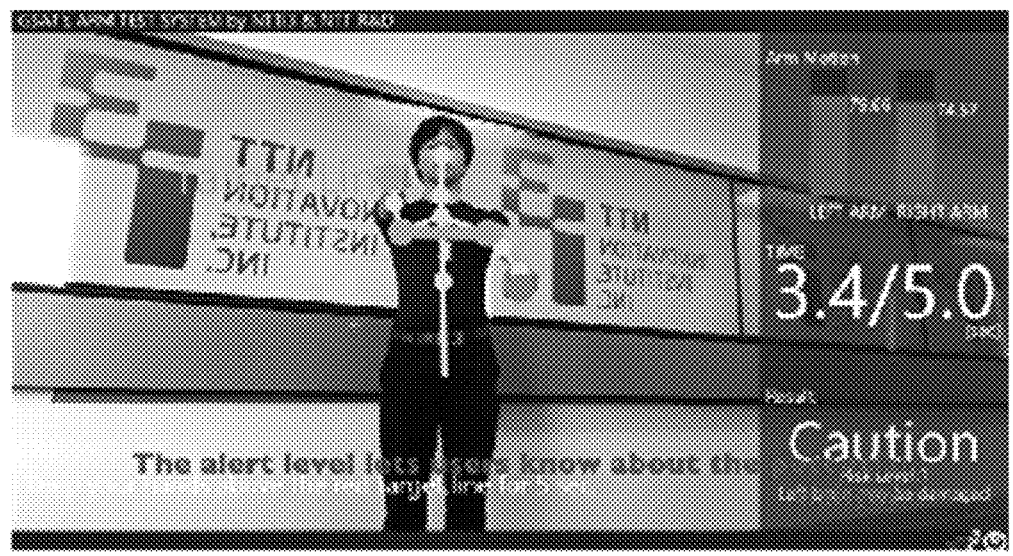
Figure 12:
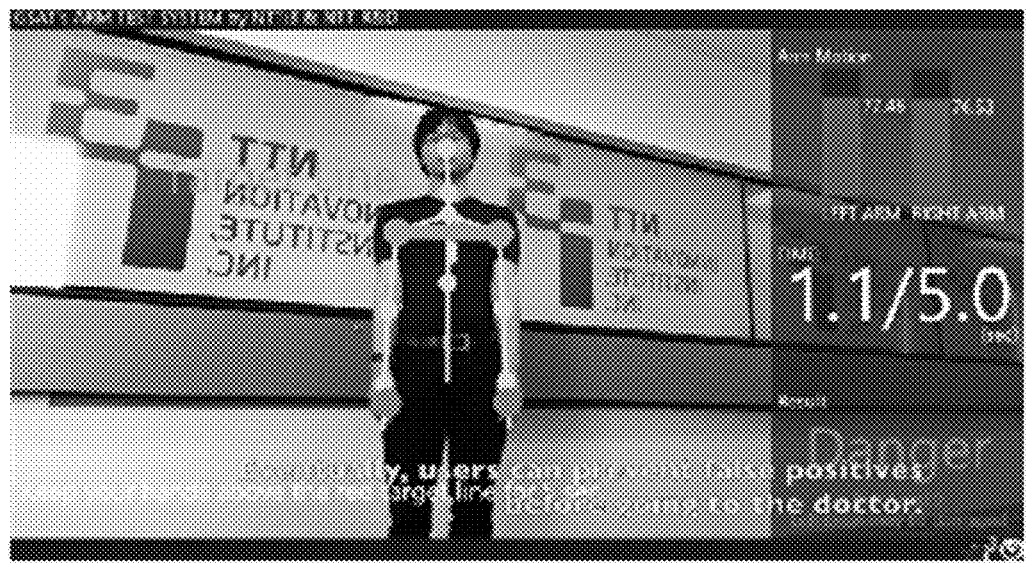

For example, as shown in FIG. 9, the device 114, such as a Microsoft Kinect, can identify the body posture. In the test, if the hand moves above the shoulder line (bold red line), the timer starts. If the user hand stays above the shoulder line for 5 seconds, no action is necessary as shown in FIG. 10 user interface. However, in the case shown in FIG. 11, the left arm of the patient drops in less than 5 seconds, which could be a stroke symptom. The right side of the brain might be impaired. In the example in FIG. 12, both arms drop in less than 5 seconds, it could be dangerous sign. The system 100 must immediately notify the primary care physician for administration of telemedicine. In this case shown in FIG. 12, the system 100 guides the user to Phase 3 (Telemedicine).

Telemedicine

Figure 13:
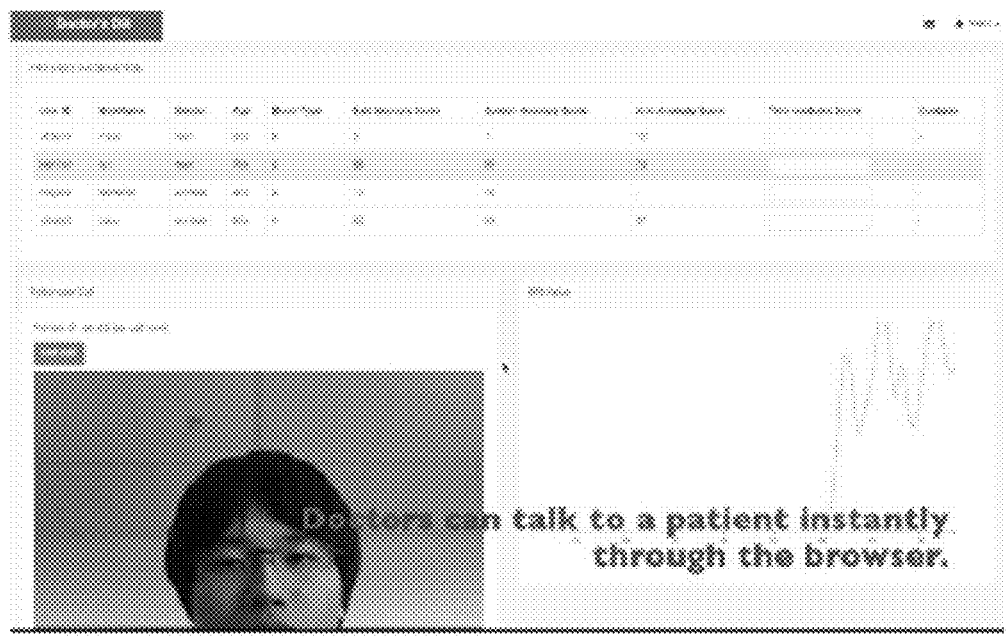
FIGS. 13-15 illustrate examples of the user interface of the telemedicine portion of the stroke detection and prevention system.

In telemedicine all of the scores computed by the data analytic services described above may be delivered to the assigned primary care physicians through dashboards such as that shown in FIG. 13. A dashboard enables doctors to monitor the status of patients in real time. If doctors think that a patient is in danger of having a stroke, they can initiate a web-based videoconference with the patient by using webRTC as shown in FIG. 13. If the patient uses wearable sensors, data such as ECG is delivered to the doctors in real time during the videoconference. Videoconferencing allows the doctors to observe not only the gait, speech, and arm movement of patients, but also their facial expressions, which can provide further evidence of stroke symptoms. If doctors conclude that a patient is in danger of a stroke, the doctor can direct the patient to seek medical care in a hospital. The system 100 should allow doctors to label the data they analyze by inputting the danger levels of observed symptoms, which can be useful for future big data analysis.

For example, the system 100 aggregates and delivers the patient's data to the doctor, as agreed upon between the patient and healthcare provider as shown in FIG. 13. The data includes name, gender, age, blood type, gait anomaly score, speech anomaly score, and arm test anomaly score. The doctor may determine that a videoconference is necessary and initiates it by using webRTC.

Figure 14:
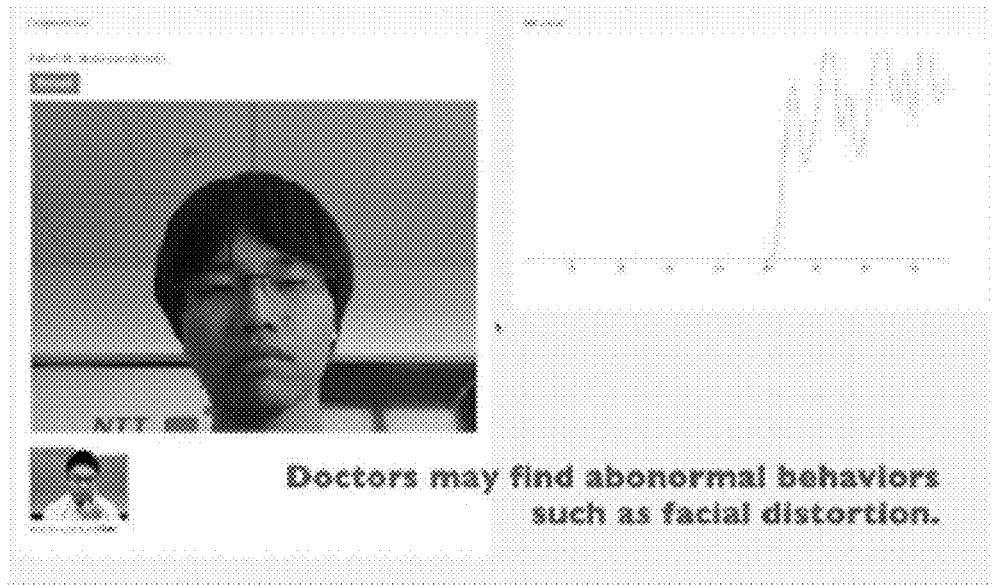
Figure 15:
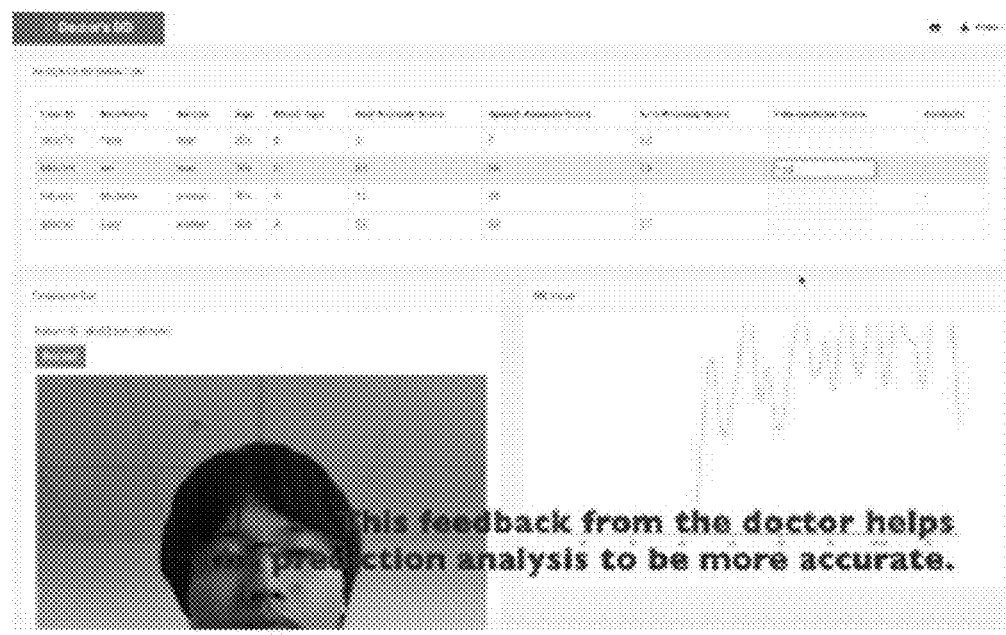

As shown in FIG. 14, during the videoconference, the doctor tests the speech of the patient and observes his facial expression. The doctor also uses his dashboard to examine data such as ECG, which is being delivered in real time. At the end of the session as shown in FIG. 15, the doctor inputs the diagnosis score. From the perspective of machine learning, it is very important that GSAT collects the data labeled by professional healthcare providers since that data can be used for the further analysis and to improve accuracy.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the disclosure and its practical applications, to thereby enable others skilled in the art to best utilize the disclosure and various embodiments with various modifications as are suited to the particular use contemplated.

The system and method disclosed herein may be implemented via one or more components, systems, servers, appliances, other subcomponents, or distributed between such elements. When implemented as a system, such systems may include and/or involve, inter alia, components such as software modules, general-purpose CPU, RAM, etc. found in general-purpose computers. In implementations where the innovations reside on a server, such a server may include or involve components such as CPU, RAM, etc., such as those found in general-purpose computers.

Additionally, the system and method herein may be achieved via implementations with disparate or entirely different software, hardware and/or firmware components, beyond that set forth above. With regard to such other components (e.g., software, processing components, etc.) and/or computer-readable media associated with or embodying the present inventions, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, handheld or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the system and method may be achieved via or performed by logic and/or logic instructions including program modules, executed in association with such components or circuitry, for example. In general, program modules may include routines, programs, objects, components, data structures, etc. that perform particular tasks or implement particular instructions herein. The inventions may also be practiced in the context of distributed software, computer, or circuit settings where circuitry is connected via communication buses, circuitry or links. In distributed settings, control/instructions may occur from both local and remote computer storage media including memory storage devices.

The software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, however no media of any such type herein includes transitory media. Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the disclosure may be implemented via computer-hardware, software and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

While the foregoing has been with reference to a particular embodiment of the disclosure, it will be appreciated by those skilled in the art that changes in this embodiment may be made without departing from the principles and spirit of the disclosure, the scope of which is defined by the appended claims.

The invention claimed is:

1. A stroke detection and prevention system, comprising:
a stroke detection and prevention computer system having a processor and a memory;
one or more computing devices that provide a first type of stroke detection data, a second type of stroke detection data and a third type of stroke detection data to the stroke detection and prevention computer system;
the stroke detection and prevention computer system memory further comprising:
a first phase element having a plurality of lines of computer code executed by the processor that performs a first phase of stroke detection comprising analyzing data from two tests performed by a user that generate the first type of stroke detection data to generate a first set of low accuracy stroke detection data, generating a stroke risk score based on the analyzing, and prompting a user to generate the second type of stroke detection data if a risk of stroke is detected;
the second phase element having a plurality of lines of computer code executed by the processor that performs a second phase of stroke detection comprising analyzing data from a test that generates the second set of higher accuracy stroke detection data, generating a stroke risk score based on the analyzing, and prompting the user to generate the third type of stroke detection data if a risk of stroke is detected; and
the third phase element having a plurality of lines of computer code executed by the processor that performs a third phase of stroke detection that processes the third type of stroke detection data obtained via telemedicine to generate a third set of highest accuracy stroke detection data.

2. The system of claim 1, wherein the first phase element further comprises a gait analysis tool that receives gait data and a speech analysis tool that receives speech data wherein the gait data and the speech data are a first type of health data.

3. The system of claim 2, wherein the gait analysis tool is configured to receive arm movement data about a user and gait data about the user and generate the first set of low accuracy stroke detection data based on the arm movement data and the gait data.

4. The system of claim 3, wherein the computing device that generates the first type of stroke detection data is a wearable health device.

5. The system of claim 4, wherein the gait analysis tool is further configured to calculate an anomaly score to determine the risk of stroke.

6. The system of claim 5, wherein the gait analysis tool is further configured to calculate the anomaly score, s, equal to ⅓ *(x+y+z) wherein x measures body balance, y measures arm swing and z measures walking cadence.

7. The system of claim 1, wherein the second phase element further comprises an arm strength test.

8. The system of claim 7, wherein the computing device that generates the second type of stroke detection data is a game device.

9. The system of claim 1, wherein the computing device that generates the third type of stroke detection data is one of a laptop computer, a personal computer and a tablet computer.

10. A stroke detection and prevention method, comprising:
receiving stroke detection data from at least one computing device that captures a first type of health data;
performing a first phase of stroke detection using a first service and a first data analysis module that processes the first type of health data to generate a first set of low accuracy stroke detection data by analyzing data from two tests performed by a user and prompts the user to generate a second type of stroke detection data if a risk of stroke is detected;
receiving stroke detection data from at least one computing device that captures the second type of health data;
performing a second phase of stroke detection using a second service and a second data analysis module that processes the second type of health data to generate a second set of higher accuracy stroke detection data and prompts the user to generate a third type of stroke detection data if a risk of stroke is detected; and
receiving stroke detection data from at least one computing device that captures the third type of health data via telemedicine;
performing a third phase of stroke detection using a third service that processes the third type of health data to generate a third set of highest accuracy stroke detection data.

11. The method of claim 10, wherein performing the first phase of stroke detection further comprises performing a gait analysis with gait data and speech analysis with speech data wherein the gait data and the speech data are the first type of health data.

12. The method of claim 11, wherein performing the gait analysis further comprising receiving arm movement data about a user and gait data about the user and generating the first set of low accuracy stroke detection data based on the arm movement data and the gait data.

13. The method of claim 12 further comprising receiving the first type of health data from a wearable health device.

14. The method of claim 13, wherein performing the gait analysis further comprises calculating an anomaly score to determine the risk of stroke.

15. The method of claim 14, wherein calculating the anomaly score further comprises calculating the anomaly score, s, equal to ⅓ *(x+y+z) wherein x measures body balance, y measures arm swing and z measures walking cadence.

16. The method of claim 10, wherein performing the second phase of stroke detection further comprises performing an arm strength test.

17. The method of claim 16 further comprising receiving the second type of health data from a game device.

18. The method of claim 11 further comprising receiving the third type of health data from one of a laptop computer, a personal computer and a tablet computer.

* * * * *